United States Patent
Hobbs (10) Patent No.: US 8,727,231 B2
(45) Date of Patent: May 20, 2014

(54) SEALED MICROFLUIDIC CONDUIT ASSEMBLIES AND METHODS FOR FABRICATING THEM

(75) Inventor: Steven Edward Hobbs, Pleasanton, CA (US)

(73) Assignee: DH Technologies Development Pte. Ltd., Singapore (SG)

( * ) Notice: Subject to any disclaimer, the term of this patent is extended or adjusted under 35 U.S.C. 154(b) by 424 days.

(21) Appl. No.: 13/299,506

(22) Filed: Nov. 18, 2011

(65) Prior Publication Data

US 2013/0126021 A1    May 23, 2013

(51) Int. Cl.
*B05B 17/00*    (2006.01)

(52) U.S. Cl.
USPC ........ 239/1; 239/589; 239/DIG. 19; 156/267; 156/293; 156/304.2; 422/70; 422/502; 264/319; 264/263; 264/267; 285/328

(58) Field of Classification Search
USPC ......... 239/1, 575, 589, DIG. 19; 422/70, 502, 422/503; 264/319, 320, 261, 263, 267; 156/267, 293, 304.2; 285/328
See application file for complete search history.

(56) References Cited

U.S. PATENT DOCUMENTS

| | | | |
|---|---|---|---|
| 6,319,476 B1 * | 11/2001 | Victor et al. | 422/502 |
| 6,481,648 B1 * | 11/2002 | Zimmermann | 239/589 |
| 2008/0216951 A1 | 9/2008 | Cyr et al. | |
| 2009/0090174 A1 | 4/2009 | Paul et al. | |
| 2010/0000927 A1 * | 1/2010 | Beigel et al. | 264/320 |
| 2010/0209302 A1 | 8/2010 | Krummen et al. | |
| 2011/0018259 A1 | 1/2011 | Arnold et al. | |

* cited by examiner

*Primary Examiner* — Steven J Ganey
(74) *Attorney, Agent, or Firm* — Bella Fishman (57) ABSTRACT

A sealed microfluidic conduit assembly is fabricated by forming a joint through which a first conduit fluidly communicates with a second conduit, by bringing the first conduit into contact with the second conduit. A layer of malleable material surrounding one or both conduits is compressed against the joint to fluidly seal the joint, by applying a radial force to an outer surface of a jacket surrounding the conduits and malleable layer. The respective compositions and/or sizes of the first conduit and second conduit may be different.

22 Claims, 5 Drawing Sheets

SEALED MICROFLUIDIC CONDUIT ASSEMBLIES AND METHODS FOR FABRICATING THEM

TECHNICAL FIELD

This present invention generally relates to connecting fluid conduits together, particularly in microfluidic applications.

BACKGROUND

Microfluidic applications often require fluid-tight connections to be made between two initially separate conduits. Conventional techniques for connecting conduits include the use of ferrules and other types of machined fittings, and certain adhesives such as UV-curable adhesives. Many problems attend conventional fluid connections, particularly in microfluidic applications. Machined fittings such as ferrules tend to be bulky and thus are often not suitable for applications requiring installation in tight spaces. Machined fittings and adhesives typically do not provide an acceptably long enough service life in microfluidic applications involving very high fluid pressures, such as HPLC (high-performance liquid chromatography). Machined fittings and adhesives typically cannot provide robust connections between two conduits made from dissimilar materials or two conduits of different sizes.

Additionally, machined fittings and adhesives may not provide fluidic connections of acceptable sealing integrity in low-flow (micro-scale or nano-scale flow) applications, which require conduits having inside diameters on the order of tens of microns. Conduits on this scale are particularly desirable in low-flow analytical separation systems such as low-flow HPLC systems, and in low-flow ionization devices utilized in atmospheric pressure ionization (API) such as small-scale electrospray probes (which may be coupled to HPLC systems). Low-flow regimes require small cross-sectional flow areas to ensure that sharp, highly discernable (low dispersion) signal peaks will be produced from analytes carried in the fluid flow. Fluid connections employed in such applications should be configured to ensure high peak resolution.

Therefore, there is an ongoing need for improved fluid connections between conduits, particularly in microfluidic applications, and for devices and assemblies employing such connections.

SUMMARY

To address the foregoing problems, in whole or in part, and/or other problems that may have been observed by persons skilled in the art, the present disclosure provides methods, processes, systems, apparatus, instruments, and/or devices, as described by way of example in embodiments set forth below.

According to one embodiment, a method for fabricating a sealed microfluidic conduit assembly includes forming a joint through which a first conduit fluidly communicates with a second conduit by bringing a first axial end section of the first conduit into contact with a second axial end section of the second conduit, wherein a layer of malleable material coaxially surrounds the first axial end section, a jacket coaxially surrounds the layer of malleable material, the first axial end section and the second axial end section, and the layer of malleable material has a lower hardness than the first conduit, the second conduit and the jacket; and compressing the layer of malleable material against the joint to fluidly seal the joint, by applying a radial force to an outer surface of the jacket at an axial distance from the joint, wherein the layer of malleable material forms a fluidic seal.

According to another embodiment, forming the joint includes bringing the first axial end section into contact with a first side of a filter and bringing the second axial end section into contact with an opposing second side of the filter.

According to another embodiment, the joint formed between the first conduit and the second conduit is a first joint, and the method further includes forming a second joint between the first conduit and a third conduit axially opposite the second conduit, and compressing the layer of malleable material against the second joint by applying a radial force to the outer surface of the jacket at an axial distance from the second joint.

According to another embodiment, a flow module includes a sealed microfluidic conduit assembly fabricated according to any of the methods disclosed herein, and a pressure sensor fluidly communicating with the sealed microfluidic conduit assembly. The inside diameter of the first conduit is less than that of the second conduit and the third conduit.

According to other embodiments, a sealed microfluidic conduit assembly is provided. The sealed microfluidic conduit assembly may be fabricated according to any of the methods disclosed herein.

According to another embodiment, an electrospray probe includes a sealed microfluidic conduit assembly in which the first conduit is composed of an electrically conductive material. The sealed microfluidic conduit assembly may be fabricated according to any of the methods disclosed herein.

Other devices, apparatus, systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The invention can be better understood by referring to the following figures. The components in the figures are not necessarily to scale, emphasis instead being placed upon illustrating the principles of the invention. In the figures, like reference numerals designate corresponding parts throughout the different views.

DETAILED DESCRIPTION

As used herein, the term "microfluidic conduit" generally refers to a conduit (tube, capillary, etc.) having an inside diameter no greater than about 2 mm. In practice, the inside diameter of a microfluidic conduit may range from about 0.01 mm to about 2 mm. Microfluidic conduits are commercially available in different inside diameters such as, for example, 0.025 mm, 0.05 mm, 0.15 mm, 0.2 mm, 0.3 mm, etc. More generally, a microfluidic conduit is sized for effectively transferring a fluid at nano-scale flow rates (nL/min) and/or micro-scale flow rates (typically up to hundreds of μL/min). In applications entailing analytical separation, the microfluidic conduit should be sized to minimize the dispersion of sample peak data. Generally, no limitation is placed on the length of a microfluidic conduit, so long as the length is sufficient for its intended purpose in a given application. A microfluidic conduit of significant length may be initially provided and thereafter cut to a desired shorter length as needed. Generally, no limitation is placed on the outside diameter of a microfluidic conduit, so long as the outside diameter results in a wall thickness providing the level of structural robustness required for withstanding the fluid pressures contemplated in a given application. In some applications such as micro-scale (microcolumn) HPLC, the fluid pressure may be on the order of tens of thousands of psi. For applications having a particular need for compactness, the outside diameter should not be excessively large or beyond what is needed for the fluid pressures contemplated. In some embodiments, the outside diameter of the microfluidic conduits may range from about 0.125 mm to about 2 mm. Microfluidic conduits are commercially available in different outside diameters such as, for example, 0.15, 0.36 mm, 1/32 inch (about 0.8 mm), 1/16 inch (about 1.6 mm), etc.

For convenience, the term "conduit" is used interchangeably with the term "microfluidic conduit" in the present disclosure.

For convenience, the term "diameter" (including "inside diameter" and "outside diameter") as used herein generally refers to the characteristic dimension (or size) of any cross-sectional area of a component such as a conduit, tube, capillary, sleeve, jacket, layer, coating, or the like. In typical embodiments, such components are cylindrical with circular cross-sections, such that the term "diameter" is accurately descriptive of the characteristic dimension of such components. It will be understood, however, that such components may alternatively have elliptical or polygonal cross-sections. The characteristic dimension of an elliptical cross-section may be considered as being a major axis. The characteristic dimension of a polygonal cross-section may be considered as being a dominant length or width of a side, or the distance between two opposing corners. The term "diameter" as used herein encompasses all such types of characteristic dimension, regardless of the actual shape of the cross-section, and thus is not intended to limit any given component to having a circular cross-section.

Figure 1A:
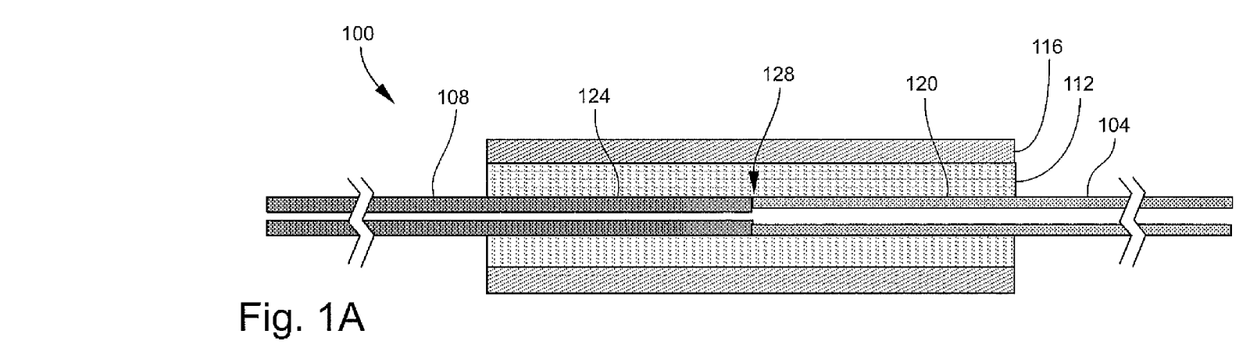
FIG. 1A is a cross-sectional view of an example of a microfluidic conduit assembly according to one embodiment, prior to completion of the assembly.

FIG. 1A is a cross-sectional view of an example of a microfluidic conduit assembly 100 according to one embodiment, prior to completion of the assembly (particularly, before applying radial compression as described below). The microfluidic conduit assembly 100 generally includes a first conduit 104, a second conduit 108, a layer 112 of malleable material (or malleable layer 112), and a jacket 116. In a typical example, the foregoing components are each cylindrical.

The first conduit 104 and the second conduit 108 may be composed of an electrically conductive material (e.g., a metal such as stainless steel) or an electrically insulating material. In the context of the present disclosure, the term "electrically insulating material" encompasses dielectric materials. Non-limiting examples of electrically insulating materials include ceramics such as fused silica, composite materials such as fused silica sheathed or coated with a polymer such as PEEK (polyether ether ketone) (e.g., PEEKsil™ tubing), and certain polymers having a hardness capable of withstanding the assembly process described below. The first conduit 104 and the second conduit 108 may have the same or different compositions. The first conduit 104 and the second conduit 108 may be microfluidic conduits having dimensions such as described above. In the present embodiment, the outside diameters of the first conduit 104 and the second conduit 108 are the same or substantially the same (e.g., differ by 0.02 mm or less). In other embodiments such as described below, the outside diameters of the first conduit 104 and the second conduit 108 are different. The inside diameters of the first conduit 104 and the second conduit 108 may be the same or different.

The malleable layer 112 may be composed of any material that is sufficiently malleable when subjected to radial compression in accordance with the method described below, and which has a hardness that is less than the respective hardnesses of the first conduit 104, the second conduit 108, and the jacket 116. In the present context, the term "radial" refers to a direction orthogonal to the longitudinal axis along which the first conduit 104 and the second conduit 108 are oriented. Also in the present context, the property of "hardness" may be quantified in accordance with any generally acceptable standard, for example Rockwell Hardness testing according to current standards promulgated by ASTM International. As an example of malleability in the present context, the malleable layer 112 is capable of being dilated (or "squeezed") between the jacket 116 and the first conduit 104 and/or second conduit 108 when subjected to radial compression. A few examples of the material utilized for the malleable layer 112 include, but are not limited to, polymers or engineering plastics such as PEEK and polyimide. In the present context, the term "polymer" encompasses co-polymers and polymer blends. Hence, a PEEK (or polyimide) polymer may encompass a polymer exclusively comprising PEEK (or polyimide), or a co-polymer or polymer blend that includes PEEK (or polyimide). In some embodiments, the initial thickness (in the radial direction) of the wall of the malleable layer 112 prior to radial compression ranges from 0.010 mm to 1 mm.

The jacket 116 may be composed of any hard material capable of withstanding the assembly process described below. In typical embodiments 116, the jacket is a metal such as stainless steel. In some embodiments, the axial length of the jacket 116 ranges from 1 mm to 100 mm.

According to one embodiment, the microfluidic conduit assembly 100 is fabricated as follows. The first conduit 104 and the second conduit 108, or more particularly a first axial end section 120 of the first conduit 104 and a second axial end section 124 of the second conduit 108, are brought into contact with each other at their respective axial ends so as to form a joint (i.e., a butt joint) 128. The first conduit 104 and the second conduit 108 are brought into contact in an aligned manner such that the interior of the first conduit 104 fluidly communicates with the interior of the second conduit 108 through the joint 128. In the present context, the term "joint" generally refers the interface or boundary of the two axial ends after they are brought into contact with each other. In some embodiments, the malleable layer 112 is provided in the form of a sleeve which, upon forming the joint 128, contacts the first conduit 104 and the second conduit 108. The sleeve may coaxially surround the first axial end section 120 and/or the second axial end section 124. In the present embodiment in which the first conduit 104 and the second conduit 108 have the same or substantially the same outside diameters, the sleeve coaxially surrounds both the first axial end section 120 and the second axial end section 124. Thus, in the present embodiment the joint 128 may be formed by inserting the malleable layer 112 into the jacket 116, and inserting the first axial end section 120 and the second axial end section 124 into the opposing axial ends of the malleable layer 112 until they come into contact with each other (i.e., abut each other). The joint 128 is then fluidly sealed (sealed so as to form a fluid-tight joint) by implementing a radial compression technique, as will now be described.

Figure 1B:
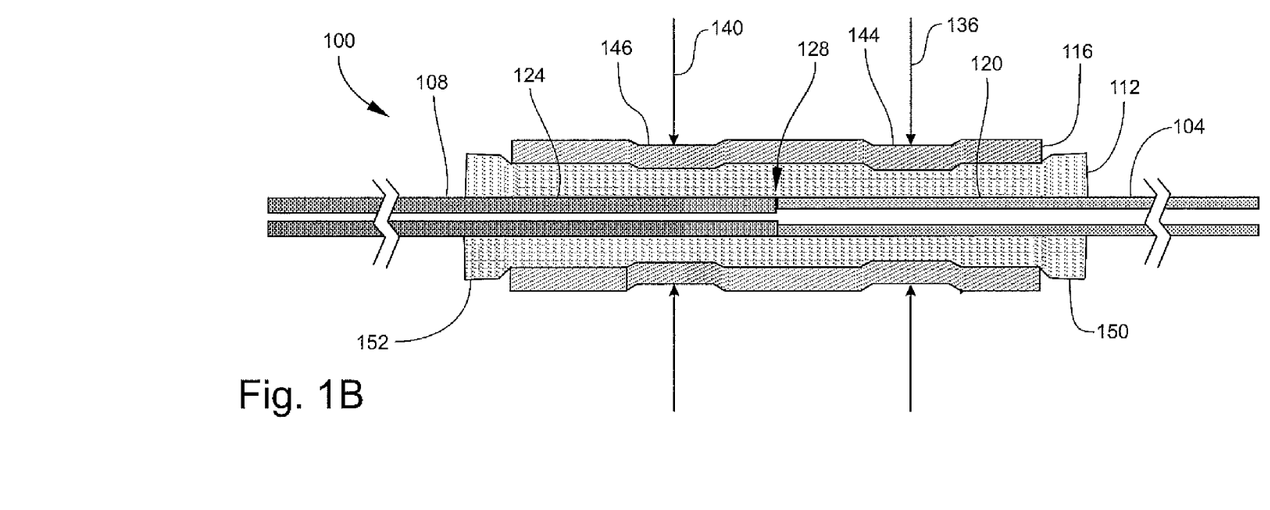
FIG. 1B is a cross-sectional view of the microfluidic conduit assembly after completion of the assembly.

FIG. 1B is a cross-sectional view of the microfluidic conduit assembly 100 after completion of the assembly, i.e. after applying radial compression. Radial compression is applied by applying a radial force to an outer surface of the jacket 116 at an axial distance from the joint 128. In the present embodiment in which the first conduit 104 and the second conduit 108 have the same or substantially the same outside diameters, a first radial force 136 may be applied at a first axial position located at an axial distance from the joint 128 (i.e., at a location of the outer surface that is radially aligned with the first axial end section 120), and a second radial force 140 may be applied at a second axial position located at an axial distance from the joint 128 (i.e., at a location of the outer surface that is radially aligned with the second axial end section 124, on the opposite side of the joint 128 relative to the first axial position). As schematically indicated by the arrows in FIG. 1B, at the respective axial positions, the radial forces 136, 140 may each be applied at a plurality of circumferential locations around the outer surface of the jacket 116. For simplicity, FIG. 1B illustrates the first radial force 136 being applied at two diametrically opposite locations on the jacket 116 at the first axial position, and the second radial force 140 being applied at two diametrically opposite locations on the jacket 116 at the second axial position. It will be understood, however, that the radial forces 136, 140 may each be applied at more than two locations around the circumference at the respective axial positions. Moreover, the radial forces 136, 140 need not be applied at localized points of contact on the outer surface of the jacket 116. That is, the tool utilized to apply the radial force 136, 140 (such as, for example, a segmented collet) may be structured to spread the radial force 136, 140 over two or more contiguous sections of the outer surface with some degree of uniformity. Moreover, the radial forces 136, 140 need not be applied symmetrically around the circumference of the jacket 116. That is, the multiple locations on the outer surface to which the radial force 136, 140 is applied need not be equally circumferentially spaced from each other.

In all such cases, the application of the radial forces 136, 140 causes the jacket 116 to bear against the malleable layer 112, as depicted in FIG. 1B by deflected sections 144, 146 of the jacket 116, thereby radially compressing (or "squeezing") the malleable material 112 between the jacket 116 and the first axial end section 120 and the second axial end section 124. In response to this radial compression, the malleable material is extruded in all directions in which it is able to "flow." In particular, the malleable material is compressed against the joint 128, thereby filling in any space existing between the interface of the respective axial ends of the two conduits 104 and 108. The effect of this radial compression is to create a permanent, fluid-tight seal around the joint 128. The resulting seal has been found to be very effective particularly in conduits of small-bore or capillary sizes. For example, in microfluidic conduit assemblies fabricated from millimeter-scale conduits, the sealed joint 128 has been found to be capable of withstanding fluid pressures of greater than 10,000 psi without failure. In some evaluations, the integrity of the fluid seal in these microfluidic conduit assemblies was maintained at pressures as high as about 60,000 psi.

As also shown in FIG. 1B, the malleable material is extruded in an axial direction through the annular space between the jacket 116 and the conduits 104 and 108. Depending on the amount of malleable material provided and the amount of force applied in a given embodiment, portions 150 and 152 of the malleable material may be extruded out from axial ends of the jacket 116. The extruded portions 150 and 152 may, if desired, be removed from the microfluidic conduit assembly 100 by any suitable means (e.g., cutting). In typical embodiments, extrusion out from the axial ends of the jacket 116 is not necessary for ensuring that an adequate fluidic seal is formed.

In some embodiments, the axial length of the jacket 116 ranges from 1 mm to 100 mm. Generally, the initial or nominal axial length of the malleable layer 112 (i.e., before compression) may be the same as the axial length of the jacket 116 as illustrated in FIG. 1A, or alternatively may be greater than or less than the axial length of the jacket 116.

The application of radial compression illustrated in FIG. 1B may be implemented in a variety of ways. In one example, a split collet (divided into two or more segments) may be placed around the jacket 116 and may be configured to apply radial force at several points on the jacket 116. Radial force may be subsequently applied to additional points by rotating the jacket 116 relative to the collet and repeating the application of the radial force. In another example, a rotary swaging or tube swaging technique may be employed. In all such cases, it can be seen that conventional ferrules and compression fittings are not required in the fabrication of the sealed microfluidic conduit assembly 100 disclosed herein. Adhesives are also not required.

As noted above, in some embodiments one or both conduits 104, 108 may be initially provided in a composite form in which the conduit 104, 108 has an outer coating of a malleable material (e.g., PEEKsil™ tubing). The thickness of the malleable outer coating may range, for example, from 0.01 to 1 mm. Such composite conduits may be utilized in conjunction with the malleable layer 112 in the fabrication of the sealed microfluidic conduit assembly 100 described above. The malleable outer coating will be radially compressed and extruded in generally the same manner as the malleable layer 112. The respective malleable outer coatings of the first conduit 104 and the second conduit 108 will be axially extruded into each other in the vicinity of the joint 128, and the respective malleable outer coatings each may contribute to sealing the joint 128. Upon application of the radial compressive forces, the malleable layer 112 and the respective malleable outer coatings may to some degree merge into each other, in the sense that the initial boundaries between these materials may no longer be discernable or at least much less discernable.

In some embodiments, both conduits 104 and 108 may be initially provided in a composite form in which the conduits 104 and 108 each have an outer coating of a malleable material. The thickness and amount of malleable material so provided may be sufficient for use in fabricating the sealed microfluidic conduit assembly 100, such that an additional layer of malleable material is not needed. FIGS. 1A and 1B may be considered as depicting these embodiments, with the malleable layer 112 representing the respective malleable outer coatings of the first conduit 104 and the second conduit 108. In these embodiments, the first conduit 104 and the second conduit 108 may be brought into contact with each other by inserting them through the opposite ends of an appropriately sized jacket 116.

In other embodiments, more than two conduits may be connected together in series by providing multiple sealed joints in accordance with any of the methods described herein.

A sealed microfluidic conduit assembly 100 such as illustrated in FIG. 1B may be utilized in any microfluidic application requiring a sealed joint between two distinct conduits. Examples include, but are not limited to, microfluidic chips, labs-on-a-chip, micro-total analysis systems (μ-TAS), microelectromechanical systems (MEMS), and micro-scale and nano-scale fluid mixers, dilutors, fluid introduction or dispensing devices, spectroscopic flow cells, and HPLC systems. The sealed microfluidic conduit assembly 100 may be particularly useful in applications requiring compact microfluidic connections for installation in tight spaces, applications requiring high-pressure microfluidic connections, and applications entailing analytical separation and thus requiring minimal signal/peak dispersion. The sealed microfluidic conduit assembly 100 generally may be deployed in substitution of the more expensive and bulky machined fittings typically associated with conventional fluid connections. Moreover, the methods of fabrication disclosed herein may be readily scaled up to produce sealed microfluidic conduit assemblies 100 at low cost. For many applications, the low cost, reliability and disposability of the sealed microfluidic conduit assembly 100 may be considered advantageous over a more expensive fluidic connection that requires service to extend useful life and avoid replacement. Additionally, the sealed microfluidic conduit assembly 100 is useful in analytical systems in which liquid sample flow should be performed with minimal dead volume and dispersion.

Also, the method for fabricating the microfluidic conduit assembly 100 is highly compatible for connecting two conduits composed of different materials. For many applications, this allows the benefits of both types of materials to be realized. For example, fused silica tubing can provide very tight inside diameter tolerances, but can be fragile and is non-conductive. On the other hand, stainless steel is very robust and conductive, but can have very large inside diameter tolerances. A connection made between a fused silica conduit and a metal conduit may allow the microfluidic conduit assembly 100 to be made with precise diameter tolerances and strong ends. Precise diameter tolerances allow devices to be manufactured in with reproducible specifications such as dispersion and flow impedance.

Figure 2A:
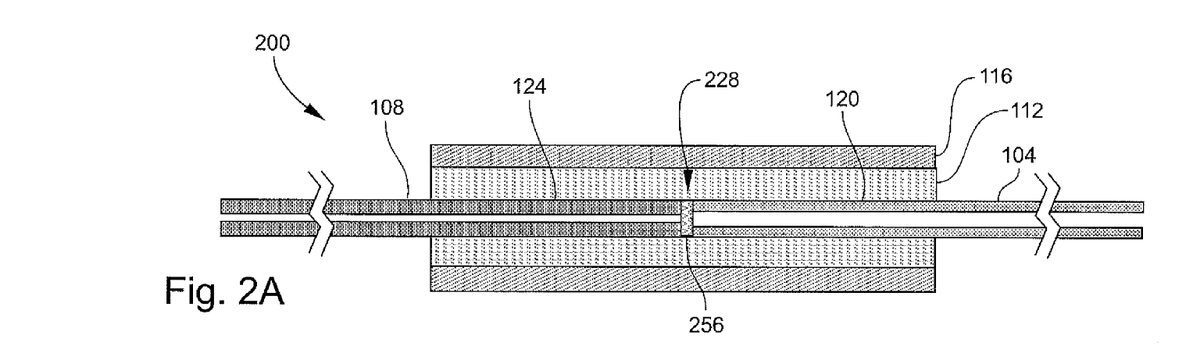
FIG. 2A is a cross-sectional view of an example of a microfluidic conduit assembly according to another embodiment, prior to completion of the assembly.
Figure 2B:
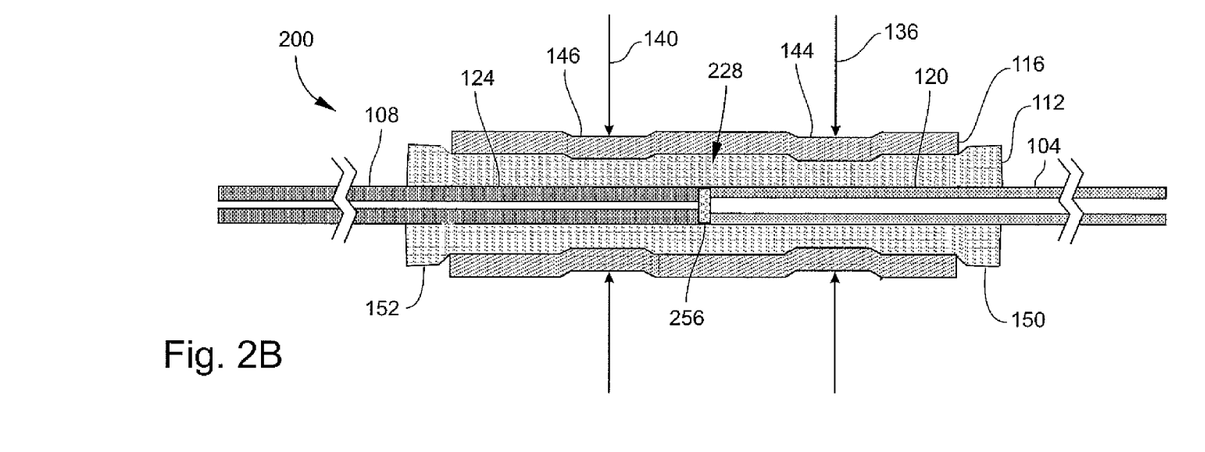
FIG. 2B is a cross-sectional view of the microfluidic conduit assembly after completion of the assembly.

FIG. 2A is a cross-sectional view of an example of a microfluidic conduit assembly 200 according to another embodiment, prior to completion of the assembly (particularly, before applying radial compression). FIG. 2B is a cross-sectional view of the microfluidic conduit assembly 200 after completion of the assembly, i.e., after applying radial compression. Some of the features or components of the microfluidic conduit assembly 200 may be the same as or similar to those of the microfluidic conduit assembly 100 described above and illustrated in FIGS. 1A and 1B, and accordingly are designated by the same or similar reference numerals in FIGS. 2A and 2B. The microfluidic conduit assembly 200 includes a filter 256 axially interposed between the first conduit 104 and the second conduit 108. Hence, in this embodiment a joint 228 is defined by the interface between the first conduit 104 and the filter 256 and the interface between the second conduit 108 and the filter 256. In typical embodiments, the filter 256 is disk-shaped as illustrated. The filter 256 may have any type of configuration, such as a mesh filter or a porous fit as appreciated by persons skilled in the art. In this embodiment, the joint 228 is formed by bringing the first conduit 104 into contact with the filter 256 on one side and the second conduit 108 into contact with the filter 256 on the opposite side. The malleable layer 112 may be provided as a sleeve, or alternatively as a coating or sheathing around one or both conduits 104, 108, as described above.

A sealed microfluidic conduit assembly 200 such as illustrated in FIG. 2B may be utilized in any microfluidic application requiring a sealed joint between two distinct conduits such as the examples noted above in conjunction with the sealed microfluidic conduit assembly 100, and additionally requiring particle filtration. As examples, the sealed microfluidic conduit assembly 200 may be employed in the input line to or output line from a fluid pump, or as a pre-column filter located upstream from an HPLC analytical column. In another example, the sealed microfluidic conduit assembly 200 may be adapted for use as the input end and/or output end (e.g., in the end cap) of an analytical column. In this case, the filter 256 may serve as the frit that retains the stationary phase in a sufficiently packed condition in the analytical column while allowing the mobile phase to pass through the analytical column. The sealed microfluidic conduit assembly 200 may also provide one or more of the advantages noted above in conjunction with the sealed microfluidic conduit assembly 100.

Figure 3:
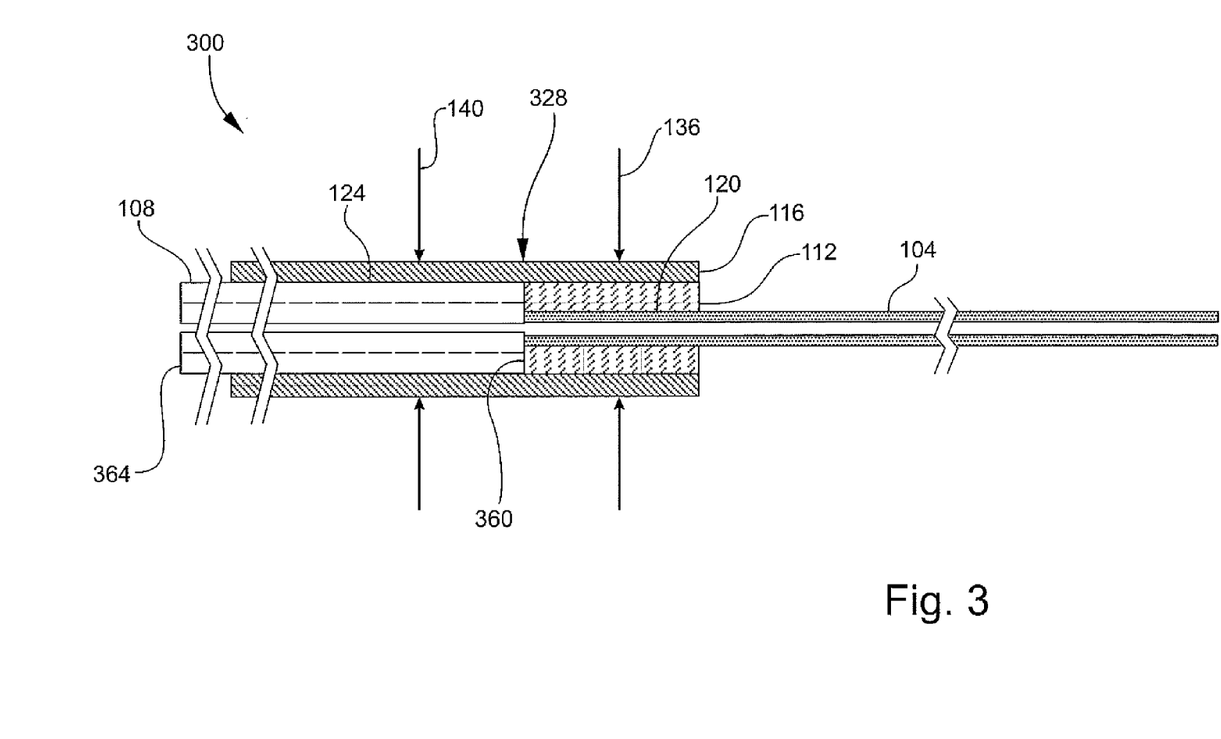
FIG. 3 is a cross-sectional view of an example of a microfluidic conduit assembly according to another embodiment.

FIG. 3 is a cross-sectional view of an example of a microfluidic conduit assembly 300 according to another embodiment. Some of the features or components of the microfluidic conduit assembly 300 may be the same as or similar to those of the microfluidic conduit assembly 100 described above and illustrated in FIGS. 1A and 1B, and accordingly are designated by the same or similar reference numerals in FIG. 3. In this embodiment, the first conduit 104 and the second conduit 108 have different outside diameters. In the example specifically illustrated, the outside diameter of the second conduit 108 is larger than that of the first conduit 104. The inside diameters of the first conduit 104 and the second conduit 108 may be the same or different. The malleable layer 112 may be provided in the form of a sleeve. In this embodiment, the malleable layer 112 serves the dual purpose of providing a fluidic seal-forming material and a make-up material to compensate for the differing outside diameters of the first conduit 104 and the second conduit 108. The jacket 116 is sized to closely fit around the larger-diameter second conduit 108. A joint 328 is formed by inserting the first conduit 104 into the malleable layer 112, inserting the first conduit 104 and malleable layer 112 through one axial end of the jacket 116, and inserting the second conduit 108 through the opposing axial end of the jacket 116. The respective axial ends of the first conduit 104 and the second conduit 108 are brought into abutting contact with each other within the interior of the jacket 116. At this time, the malleable layer 112 may or may not be in contact with an end face 360 of the second conduit 108.

The joint 328 is then sealed by applying a radial force 136 to the outer surface of the jacket 116 at an axial distance from the joint 328, i.e., at a first axial position that is radially aligned with the malleable layer 112 and the first axial end section 120, as schematically indicated by the arrows in FIG. 3. The radial force 136 may be applied using the same or similar techniques as described above in conjunction with FIG. 1B. Hence, the radial force 136 may be applied at a plurality of circumferential locations around the outer surface of the jacket 116, and may be applied at localized points of contact on the outer surface of the jacket 116 or over contiguous areas of the outer surface. The application of the radial forces 136 causes the jacket 116 to bear against the malleable layer 112, thereby radially compressing the malleable material between the jacket 116 and the first axial end section 120.

In response to this radial compression, the malleable material is extruded in all directions available for extrusion. As a result, the malleable material is compressed against the joint 328, filling in any space existing between the interface of the respective axial ends of the two conduits 104 and 108, thereby creating a permanent, fluid-tight seal around the joint 328. Provided with sufficient radial force, a portion (not shown) of the malleable material could be extruded out from axial end of the jacket 116 surrounding the first conduit 104 and may, if desired, be removed from the sealed microfluidic conduit assembly 300.

In some implementations, the malleable layer 112 may represent a coating or sheathing initially provided with the first conduit 104.

In some implementations, a second malleable layer 364 sized to fit coaxially between the second conduit 108 and the outer jacket 116 may be provided, as schematically depicted by dashed lines in FIG. 3. The second malleable layer 364 may be a sleeve that is initially provided as component separate from the second conduit 108. Alternatively, the second conduit 108 may be provided as a composite structure that includes the second malleable layer 364 as an outer coating or sheathing. In either case, a second radial force 140 may be applied to the outer surface of the jacket 116 at a second axial position that is radially aligned with the second malleable layer 364 and the second axial end section 124, on the opposite side of the joint 328 relative to the first axial position, as schematically indicated by the arrows in FIG. 3. In this manner, radial compression of the second malleable layer 364 may contribute to sealing the joint 328.

A sealed microfluidic conduit assembly 300 such as illustrated in FIG. 3 may be utilized in any microfluidic application requiring a sealed joint between two distinct conduits such as the examples noted above in conjunction with the sealed microfluidic conduit assembly 100. The sealed microfluidic conduit assembly 300 is particularly useful in applications requiring microfluidic connections between two conduits having different outside diameters. The sealed microfluidic conduit assembly 300 may also provide one or more of the advantages noted above in conjunction with the sealed microfluidic conduit assembly 100.

In one example, the sealed microfluidic conduit assembly 300 may be utilized as, or form a part of, an electrospray probe for ionizing liquid samples in an atmospheric pressure ionization (API) interface according to the known technique of electrospray ionization (ESI). In this example, the first conduit 104 is composed of an electrically conductive material and serves as the electrospray needle (or electrospray tip). The small, compact microfluidic connection provided by sealed microfluidic conduit assembly 300 enables the electrospray probe to provide a low-dispersion fluid path.

In one non-limiting example of the electrospray probe, the first conduit 104 is 316L stainless steel tubing and has an axial length of 0.625 inch, an inside diameter of 0.002+/−0.001 inch, and an outside diameter of 0.012+/−0.005 inch. The second conduit 108 is a PEEKsil™ composite, and has an axial length of 20.0 cm, an inside diameter of 50 μm, and an outside diameter of 1/32 inch. The malleable layer 112 is PEEK or polyimide, and has an axial length of 0.15 inch and an inside diameter of 0.013 inch. The jacket 116 is 316L stainless steel tubing, and has an axial length of 0.75+/−0.02 inch, an inside diameter of 0.031+0.001/−0.005 inch, and an outside diameter of 0.042+/−0.002 inch.

Figure 4:
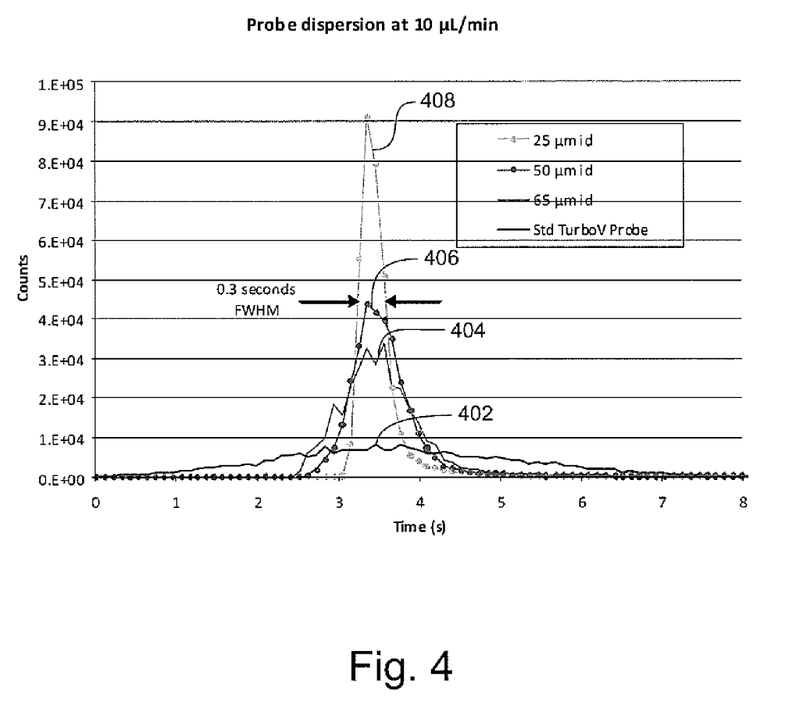
FIG. 4 is a plot of signal peaks for four different electrospray probes, two of which were fabricated in a manner consistent with the embodiment illustrated in FIG. 3.

FIG. 4 illustrates an example of the improved dispersion provided by an electrospray probe when fabricated as described above and illustrated in FIG. 3. Specifically, FIG. 4 is a plot of signal intensity (in counts) over time (in seconds) for four different electrospray probes. The needle (first conduit) of each probe was stainless steel and had a different inside diameter. Each probe was tested by flowing the same analyte sample at the same flow rate (10 μL/min). The four probes produced four peaks 402, 404, 406, 408, which are superposed on each other in FIG. 4 for comparative purposes. The first probe was a commercially available probe equipped with a needle having an inside diameter of 100 μm. The peak 402 produced by the first probe is severely smeared. The second probe was a modified version of the first probe in which the needle had an inside diameter of 65 μm. The peak 404 produced by the second probe is much less dispersed than the peak 402 produced by the first probe. The third and fourth probes were fabricated as described above and illustrated in FIG. 3, with needles having inside diameters of 50 μm and 25 μm, respectively. The peak 406 produced by the third probe is improved in comparison to the peaks 402 and 404. The peak 408 produced by the fourth is dramatically improved, exhibiting a peak width (FWHM, or full width at half maximum) of 0.3 second.

Figure 5:
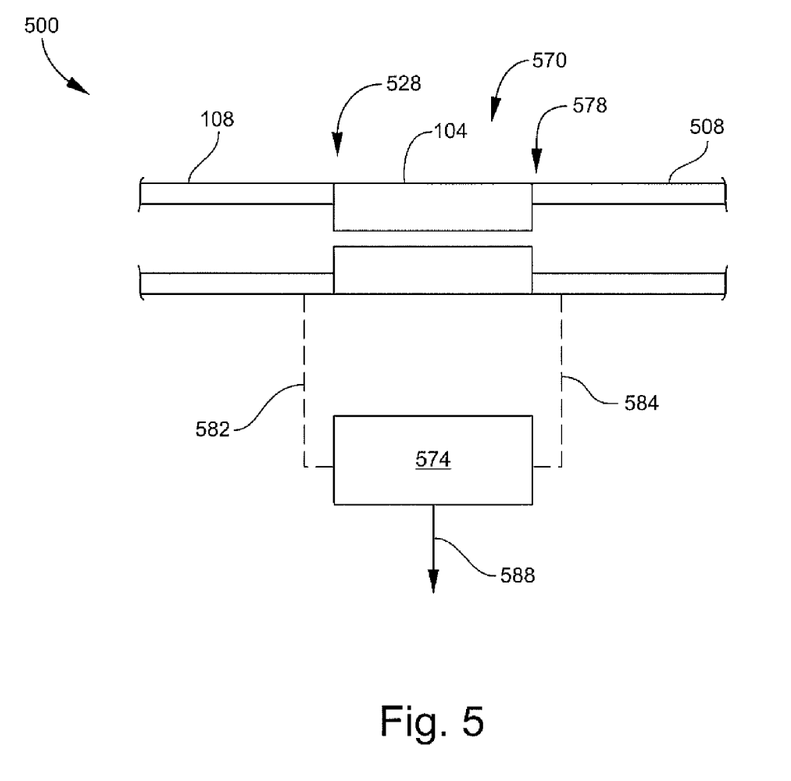
FIG. 5 is a schematic view of a flow module according to another embodiment.

FIG. 5 is a schematic view of a flow module 500 according to another embodiment. The flow module 500 generally includes a flow restrictor 570 and one or more pressure sensors 574 fluidly communicating with the flow restrictor 570. The flow restrictor 570 is a sealed microfluidic conduit assembly that includes two sealed joints axially spaced from each other so as to connect three conduits in series. Specifically, the flow restrictor 570 is defined by a first conduit 104 connected to a second conduit 108 at one axial end and to a third conduit 508 at the other axial end. The first conduit 104 is connected to the second conduit 108 by a first sealed joint 528 and to the third conduit 508 by a second sealed joint 578. The sealed joints 528 and 578 are fabricated in accordance with any of the methods described above and illustrated in FIGS. 1A-3. The malleable layer (not specifically shown) may be provided as one or more distinct components. As an example, the malleable layer may be provided as a single component having an initial axial length that spans a majority of the axial length of the first conduit 104, or is about the same as the axial length of the first conduit 104, or is longer than the first conduit 104 and overlaps with the second and third conduits 108 and 508. As another example, a first malleable layer may be provided where the first joint 528 is to be formed, and a second malleable layer may be provided where the second joint 578 is to be formed. As another example, one or more of the conduits 104, 108, 508 may include a coating or sheathing of malleable material as described above.

The first conduit 104, second conduit 108 and third conduit 508 of the flow module 570 respectively have a first inside diameter, a second inside diameter and a third inside diameter. The first inside diameter is less than the second and third inside diameters, and typically the second and third inside diameters are the same. The respective outside diameters of the first conduit 104, second conduit 108 and third conduit 508 may be the same or different. Due to its smaller inside diameter, the first conduit 104 introduces a reduced flow area in the fluid flow path defined through the first conduit 104, second conduit 108 and third conduit 508. Hence, a pressure drop is observed across the axial length of the first conduit 104, which can be correlated to the flow rate through the conduits 104, 108, 508 as appreciated by persons skilled in the art. For this purpose, fluid lines 582 and 584 from the pressure sensor(s) 574 respectively communicate with the fluid flow path near the axial ends of the first conduit 104. The fluid lines 582 and 584 may be respectively tapped into the second conduit 108 and third conduit 508 by any suitable means. The pressure sensor(s) 574 may have any suitable configuration for measuring the pressure drop. In one example, the pressure sensor 574 is a single pressure sensor is configured for measuring the pressure drop. In another example, the pressure sensor 574 includes one pressure sensor associated with one fluid line 582 for measuring the pressure at one axial end of the first conduit 104, and another pressure sensor associated with the other fluid line 584 for measuring the pressure at the other axial end of the first conduit 104. In the latter example, the two pressure readings may be compared (e.g., one reading subtracted from the other) to determine the pressure drop. An output signal 588 from the pressure sensor(s) 574 may be transmitted as a feedback signal to an electronic controller (not shown) to enable the electronic controller to control the flow rate (such as by controlling a micro-pump).

The flow module 500 may provide one or more of the advantages noted above in conjunction with the sealed microfluidic conduit assembly 100. These may include, for instance, facilitating the connection between conduits of different sizes, the connection between conduits of different material compositions, and the provision of more precise and robust flulidic connections.

It will be understood that various aspects or details of the invention may be changed without departing from the scope of the invention. Furthermore, the foregoing description is for the purpose of illustration only, and not for the purpose of limitation—the invention being defined by the claims.

What is claimed is:

1. A method for fabricating a sealed microfluidic conduit assembly, the method comprising:
   forming a joint through which a first conduit fluidly communicates with a second conduit by bringing a first axial end section of the first conduit into contact with a second axial end section of the second conduit, wherein a layer of malleable material coaxially surrounds the first axial end section, a jacket coaxially surrounds the layer of malleable material, the first axial end section and the second axial end section, and the layer of malleable material has a lower hardness than the first conduit, the second conduit and the jacket; and
   compressing the layer of malleable material against the joint to fluidly seal the joint, by applying a radial force to an outer surface of the jacket at an axial distance from the joint, wherein the layer of malleable material forms a fluidic seal.

2. The method of claim 1, wherein the first conduit and the second conduit are composed of different materials.

3. The method of claim 1, wherein one of the first conduit and the second conduit is composed of an electrically conductive material and the other is composed of an electrically insulating material.

4. The method of claim 1, wherein the jacket driver is composed of a metal and the layer of malleable material is composed of a polymer.

5. The method of claim 1, wherein the layer of malleable material comprises PEEK or polyimide.

6. The method of claim 1, wherein the first conduit and the second conduit each have an inside diameter ranging from 0.01 mm to 2 mm.

7. The method of claim 1, wherein compressing the layer of malleable material extrudes a portion of the malleable material out from an annular opening between the jacket and the first conduit, and further comprising removing the extruded portion.

8. The method of claim 1, wherein compressing the layer of malleable material comprises applying the radial force to a plurality of circumferential points around the outer surface at the axial distance.

9. The method of claim 1, wherein forming the joint comprises bringing the first axial end section into contact with a first side of a filter and bringing the second axial end section into contact with an opposing second side of the filter.

10. A sealed microfluidic conduit assembly fabricated according to the method of claim 9.

11. The method of claim 1, wherein the first conduit and the second conduit have substantially the same outer diameter, the layer of malleable material coaxially surrounds the second axial end section, and compressing the layer of malleable material extrudes the layer in a first axial direction toward a first end of the jacket and in an opposing second axial direction toward a second end of the jacket.

12. The method of claim 11, wherein applying the radial force comprises applying a first radial force to the outer surface at a first axial distance from the joint, and applying a second radial force to the outer surface at a second axial distance from the joint on an opposite side of the joint relative to the first axial distance.

13. The method of claim 11, wherein compressing the layer of malleable material extrudes respective portions of the malleable material out from the first end and the second end, and further comprising removing the extruded portions.

14. The method of claim 11, wherein the layer of malleable material is a sleeve, and forming the joint comprises inserting the first axial end section and the second axial end section into opposite ends of the sleeve.

15. The method of claim 11, wherein the layer of malleable material comprises a first portion coating the first axial end section and a second portion coating the second axial end section, and forming the joint comprises inserting the first axial end section coated with the first portion and the second axial end section coated with the second portion into opposite ends of the jacket, and compressing the layer of malleable material extrudes the first portion and the second portion into contact with each other.

16. The method of claim 11, wherein the first conduit has a smaller outer diameter than the second conduit, the layer of malleable material contacts an end face of the second conduit and is interposed between the first conduit and the jacket, and compressing the layer of malleable material comprises applying the radial force to the outer surface at a location in radial alignment with the first axial end section, wherein the layer of malleable material is compressed against the end face.

17. The method of claim 16, wherein the layer of malleable material is a sleeve, and forming the joint comprises inserting the first axial end section into the sleeve.

18. The method of claim 16, wherein the layer of malleable material comprises a coating on the first axial end section, and forming the joint comprises inserting the first axial end section with the coating into a first end of the jacket and inserting the second axial end section into an opposing second end of the jacket.

19. The method of claim 1, wherein the joint formed between the first conduit and the second conduit is a first joint, and further comprising forming a second joint between the first conduit and a third conduit axially opposite the second conduit, and compressing the layer of malleable material against the second joint by applying a radial force to the outer surface of the jacket at an axial distance from the second joint.

20. A flow module comprising a sealed microfluidic conduit assembly fabricated according to the method of claim 19, and a pressure sensor fluidly communicating with the sealed microfluidic conduit assembly, wherein an inside diameter of the first conduit is less than an inside diameter of the second conduit and the third conduit.

21. A sealed microfluidic conduit assembly fabricated according to the method of claim 1.

22. An electrospray probe comprising a sealed microfluidic conduit assembly fabricated according to the method of claim 1, wherein the first conduit is composed of an electrically conductive material.

* * * * *